(12) United States Patent
Giri (10) Patent No.: US 6,602,679 B2
(45) Date of Patent: Aug. 5, 2003

(54) STABILIZED FORMULATIONS FOR CHEMILUMINESCENT ASSAYS

(76) Inventor: Brij Giri, 36725 Lamarra Dr., Sterling Heights, MI (US) 48310

( * ) Notice: Subject to any disclaimer, the term of this patent is extended or adjusted under 35 U.S.C. 154(b) by 0 days.

(21) Appl. No.: 09/770,592

(22) Filed: Jan. 26, 2001

(65) Prior Publication Data

US 2001/0046688 A1 Nov. 29, 2001

Related U.S. Application Data (60) Provisional application No. 60/178,626, filed on Jan. 28, 2000.

(51) Int. Cl.$^7$ .................................................. C12Q 1/28
(52) U.S. Cl. ............................ 435/28; 435/25; 435/188
(58) Field of Search ................................ 435/28, 25, 4, 435/11, 14, 188

(56) References Cited

U.S. PATENT DOCUMENTS 4,950,588 A * 8/1990 Dattagupta
5,084,381 A * 1/1992 Akimoto et al.
5,705,357 A * 1/1998 Kissel et al.

FOREIGN PATENT DOCUMENTS

EP            0625510 A2 * 11/1994

* cited by examiner

Primary Examiner—Ralph Gitomer
(74) Attorney, Agent, or Firm—Plunkett & Cooney, P.C.; Arnold S. Weintraub, Esq.

(57) ABSTRACT

A substrate having an extended shelf life for chemiluminescent detection and assaying is useful with enzyme-based probes as well as for immunoassays, DNA or RNA or protein detection and blotting. The substrate is a mixture of (a) a chemiluminescent compound, (b) an oxidant, (c) a stabilizer and (d) a buffer. The substrate may further include a chemiluminescent enhancer and a solubilizer. The substrate may be in an organic solvent or may be aqueous based.

9 Claims, 11 Drawing Sheets

STABILIZED FORMULATIONS FOR CHEMILUMINESCENT ASSAYS

CROSS REFERENCE TO RELATED APPLICATION

This application is a completion application of copending U.S. provisional application Ser. No. 60/178,626, filed Jan. 28, 2000, the disclosure of which is hereby incorporated by reference.

BACKGROUND OF THE INVENTION

1. Field of the Invention

This invention relates to chemiluminescent compounds and methods of use therefor. More particularly, the present invention concerns novel stabilized chemiluminescent formulations containing all the necessary components for chemiluminescence light generation. Even more particularly, the present invention relates to a single or one-part reagent for detecting and quantifying various biological molecules through chemiluminescence as well as detecting DNA fragments in DNA sequencing applications and methods of use therefore.

2. Description of Related Art

Radioimmunoassay has provided the most practical approach to achieve detection of antigens and antibodies in picomolar concentrations and is, thereforee, widely used in both clinical and pharmacological laboratories. However, the very success and widespread use of radioimmunoassays has raised several problems which include: (1) shelf-life and stability of radiolabeled compounds, (2) high cost of radioactive waste disposal, and (3) health hazards as a result of exposure to the use of not only radioactive materials but to the solvent necessary for liquid-scintillation counting, as well.

Chemiluminescence, i.e. the production of light by chemical reaction, and bioluminescence, i.e. the light produced by some living organisms, have been tested as potential replacements for radioactive labels, not only in competitive and sandwich-type immunoassays, but also, DNA sequencing and other related research. Chemiluminescence provides a major advantage over radioactive labeling because it generates cold light i.e. its generated light is not caused by vibrations of atoms and/or molecules involved in the reaction but by direct transformation of chemicals into electronic energy. Thus, research on the chemiluminescence of organic compounds is an on-going area of major emphasis. Parenthetically, chemiluminescence is also advantageous in detecting and measuring trace elements and pollutants for environmental control. The best known chemiluminescent reactions are those which employ either stabilized enzmye triggerable 1,2-dioxetanes, acridanes, acridinium esters, luminol, isoluminol and derivatives thereof or lucigenin, as the chemical agent, reactant or substrate.

Enzymatic triggerable 1,2-dioxetanes such as those described by A. P. Schaap, R. S. Handley and B. P. Giri. *Tetrahedron Lett.*, 935 (1987); A. P. Schaap, T. S. Chen, R. S. Handley, R. DeSilva, and B. P. Giri, *Tetrahedron Lett.*, 1159 (1987) as well as in U.S. Pat. No. 5,707,550 and PCT/US99/20590 are superior in immunoassays and other related applications compared to presently known peroxidase substrates such as luminol and the like, because these 1,2-dioxetane substrates are highly sensitive and detect an enzyme concentration up to $10^{-21}$M in solution, as well as on a membrane. Futher, stabilized 1,2-dioxetane substrates provide high signal, low background, wide dynamic range, rapid results and excellent reproducibility.

On the other hand, peroxidase is widely distributed in higher plants and in especially high concentrations in fig sap and horseradish. It is also found in some animal tissues and in microorganisms. Because of its wide availability, horseradish peroxidase(HRP) is widely used in labeling haptens, antibodies, protein A/G, avidin, streptavidin and DNA for enzyme immunoassays, immunocytochemistry, immunoblot and DNA detection.

In an assay procedure, HRP is used in lieu of the enzymatic triggerable dioxetane because detection of enzyme activity takes advantage of the reactive cooperation between the enzyme and a highly sensitive chemiluminescent agent. Peroxidase-based chemiluminescent assays, while demonstrating improved detection sensitivity, suffer from the lack of reproducibility such that the obtained data is not always reliable.

According to the prior art, two problems arise in the detection of peroxidase activity. First, a HRP assay is employed as either a two component reaction system or a two step reaction process. See, inter alia U.S. Pat. Nos. 4,598,044; 5,171,668; 5,206,149; 5,552,298; 5,601,977; 5,593,845; 5,670,644; 5,723,295. The two component system provides two reagents, one reagent containing an organic compound for light production such as luminol and the second an oxidizing agent such as hydrogen peroxide. When the two are mixed together, peroxidase enzyme detection occurs. However, the resulting solution, after mixing, is not stable for a long period of time and due to the instability of the mixed reagent the background is very high. Indeed, the chemiluminescence of most of the prior art systems is like a flash or a glow for a short period of time. Further, in a two-step chemiluminescence reaction process, the first step, i.e. the peroxidase catalyzed reaction, is done at a lower pH than the second step of the reaction. This causes accumulation of an intermediate compound which is subsequently induced to produce a burst of light by raising the pH of the solution. Thus, the multistep nature of peroxidase-catalyzed luminescent reaction, with rate limiting steps and competing side reactions, creates several problems in efficiency and reproducibility when used in the immunological field. The second problem is the lost activity of the peroxidase enzyme in buffers. The stock solutions of peroxidase below 10 ng/ml are not stable, even in the presence of bovine serum albumin. For example, at 10 pg/ml, activity is lost within one minute, and even at 1 ng/ml, the solution is stable for not more than two minutes. See K. Pugnet, A. M. Michelson, and S. Avrameas, Anal. Biochem. 79 477–456 (1977). The same results are observed when peroxidase is assayed using luminol-hydrogen peroxidase as a substrate in the presence of N-methylphenothiazine and phenolindophenol as an enhancer as shown in FIG. 2 of U.S. Pat. No. 5,171,668. Furthermore, this reference shows the non-linear relationship between the concentration of a peroxidase-labeled AFP antibody and light emission.

In spite of its known deficiencies horseradish peroxidase, as noted above, is still widely used for assays because it is widely available and inexpensive to use. Horseradish peroxidase catalyzes the luminescent oxidation of a wide range of substrates including cyclic hydrazide, phenol derivatives, acridane derivatives and components of bioluminescent systems. Other suitable substrates, also, include: (a) luminol and related compounds, as taught by [L. Ewetz, and A. Thore. *Anal. Biochem.*, 71, 564 (1976), A. D. Pronovost and A. Baumgarten, *Experientia*, 38, 304 (1982), H. Arakawa, M. Maeda and A. Tsuji, *Anal. Biochem.*, 97, 248 (1979), L. S. Hersh, W. P. Vann, and S. A. Wilhelm, *Methods in Enzymology*, 73, 608 (1981)]; (b) pyrogallol, and purpurogallin as taught by [B. Velan and M. Halmann, *Immunochemistry*, 15, 331 (1978), M. Halmann, B. Velan, T. Sery and H. Schupper, *Photochem. Photobiochem.*, 30,165 (1979), G. Ahnstrom and R. Nilsson, Acta. *Chim. Scand.*, 19, 313 (1965), (c) acridanecarboxylic acid derivatives as taught by [H. Akhavan-Tafti, R. DeSilva, Z. Arghavani, R. A. Eickholt, R. S. Handley, B. A. Schoenfelner, K. Sugioka, Y. Sugioka and A. P. Schaap, *J. Org. Chem.*, 63, 930 (1998)]; and (d) luciferins isolated from *Pholas dactlus*, and the firefly *Photinus pyralis* or Cypridina as disclosed by [K. Puget, A. M. Michelson and S. Avrameas, *Anal. Biochem.*, 79, 447 (1977), D. Slawikska, J. Siwinski, W. Pukacki and K. Polewski, in "*Analytical Application of Bioluminescence and Chemiluminescence*" (E. Schram and P. Stanley, eds.), p. 239, State Publishing and Printing, Westlake Village, Calif., 1979. T. Kobayashi, K. Saga, S. Shimizu and T. Goto, *Agric. Biol. Chem.*, 46, 1403 (1981)]. These light producing reactions differ widely in their detection limits, specificity, reagent availability and magnitude and kinetics of light emission. This, of course, restricts their applicability.

As noted above, peroxidase catalyzed luminescence suffers from two problems, namely, (1) peroxidase enzyme instability at lower concentrations in a buffer, and (2) low luminescence efficiency and high background. The known literature reveals that most of the time, the second problem, can be compensated for. For example, the prior art teaches the use of a non-chemiluminescent hydrogen donor, such as o-phenylenediamine, to activate the luminescent reaction of pyrogallol. See, inter alia, Ahnstrom and Nilsson *Acta. Chim. Scand,,* 19, 313 (1966).

However, the effect of a non-chemiluminescent donor on luminescence has been found to be profoundly influenced by changes in the ratio between the luminescent donor and the non-luminescent donor. The increase of light emission caused by the addition of o-phenylenediamine is accompanied by an accelerated formation of the blue dimer, thus speeding up the rate-limiting step. At constant pyrogallol concentrations it has been found that the addition of o-phenylenediamine never causes an increase in the integrated luminescence yield, although the velocity of the luminescent process can be accelerated, thus giving a higher luminescence peak. On the other hand incorporation of p-phenylenediamine into a peroxidase-purpurogallin-hydrogen peroxide system results in an eight-fold enhancement of light emission [M. Halmann, B. Velan, T. Sery and H. Schupper, *Photochem. Photobiochem.*, 30, 165 (1979)]. The effect of other factors such as pH change, deuterated solvent, radical scavengers and the addition of other enhancers on the enhancement of chemiluminescence of peroxidase-catalyzed reactions has been reported in the literature. See, inter alia, L. Ewetz and A. Thore, Anal. Biochem., 71, 564 (1976); J. K. Wong and M. L. Salin, *Photochem. Photobiol.*, 33, 737 (1981); H. P. Misra and P. M. Squatrioto, *Arch. Biochem. Biophys.*, 215, 59 (1982); G. H. G. Thorpe, L. J. Kricka, E. Gillespie, S. Moseley, R. Amess, N. Bagget and T. P. Whitehead, Anal. Biochem., 145, 96 (1985); T. J. N. Carter, C. J. Groucutt, R. A. W. Stott, G. H. G. Thorpe and T. P. Whitehead, European Patent, No. 87959 (1982); G. H. G. Thorpe, L. J. Kricka, S. B. Moseley and T. P. Whitehead, *Clin. Chem.* (Winston-Salem, N.C.), 31, 1335 (1985); L. J. Kricka, G. H. G. Thorpe and T. P. Whitehead, European Patent No. 116454 (1983) and U.S. Pat. No. 4,598,044.

Similarly, numerous assay enhancers have been employed in conjunction with and in a peroxidase-catalyzed reaction of luminol or acridanes to increase the intensity and duration of light emission. These enhancers include benzothiazole derivatives such as 6-hydroxybenzothiazole derivatives, dehydroluciferin, firefly luciferin, substituted phenols such as p-iodiophenols, p-phenylphenol or 2-naphthol, and aromatic amines such as p-phenylenediamine or tetramethyl benzidine. Other compounds which function as enhancers for chemiluminescent oxidation of amino-substituted cyclic acylhydrazide by a peroxidase include N,N-dimethylindoaniline, 2,6-dichlorophenoline-o-cresol, phenolindophenol, N-methyl-phenathiazine and a combination of phenolindolphenol and N-methylphenathiazine as disclosed in U.S. Pat. No. 5,171,668 and Paul D. Davis, Kelli Feather-Henigan, Kimberly Hines, PCT/US97/06422 (1999).

The chemiluminescence enhancing effect of 2-hydroxy-9-fluoro-4-hydroxy-3-[3-(4-hydroxyphenyl)-1-oxo-2-propenyl]-2H-1-benzopyrene-2-one and substituted oxazole derivatives in a peroxidase-oxidant-luminol or isoluminol system has, also, been reported. See, U.S. Pat. No. 5,206, 149. Similarly, surfactants including nonionic, cationic and anionic as well as polymeric compounds are known to affect the light producing efficiency of peroxidase catalyzed reactions, as reported by L. J. Kricka and M. Deluca, *Arch. Biochem. Biophys.*, 217, 674 (1983); T. Goto and H. Fukatsu, Tet. Letts., 4299 (1969); and K. Sasamoto and Y. Ohkura, *Chem. Pharm. Bull.*, 39, 411 1991). The major advantage of enhanced assays is that the intensity of light emission may be greater than 1000-fold that of the un-enhanced reaction. Also, conditions can be employed under which light emission is prolonged and decay is slow.

The full mechanism for the oxidation of cyclic acylhydrazides and acridanes by the combination of peroxide and peroxidase enzyme and the light enhancement by enhancers is not known. However, many compounds reported to increase light emission from chemiluminescent and bioluminescent systems do not enhance the peroxidase-catalyzed system under reported conditions, but 6-hydroxybenzothiazole and phenol derivatives produce dramatic increases in light intensity, thereby suggesting they operate by a different mechanism. See, for example, (T. P. Whitehead, G. H. G. Thorpe, T. J. N. Carter, C. Groucuft and L. J. Kricka, Nature (London), 305, 158 (1983); H. W. Yurow and S. Sass, *Anal. Chim. Acta.*, 88, 389 (1977); D. E. Bause and H. H. Patterson, *Anal. Chem.*, 51, 2288 (1985); F. Kohen, J. B. Kim, G. Barnard and H. R. Linder, *Steroids,* 36, 405 (1980); H. R. Schroeder, P. O. Vogelhut, R. J. Carrico, R. C. Boguslaski and R. T. Buckler, Anal. Chem., 48, 1933 (1976), and M. L. Grayeski and E. Woolf, in "*Analytical Application of Bioluminescence and Chemiluminescence*" (L. J. Kricka, P. E. Stanley, G. H. G. Thorpe and T. P. Whitehead, eds), p. 565, Academic Press, Orlando, 1984).

The present invention as detailed hereinbelow, alleviates problems associated in the prior art by providing unique enzyme or other biological molecule-activated compounds and methods of use therefor.

SUMMARY OF THE INVENTION

The present invention provides a stable chemiluinescent formulation for use as a substrate in assaying peroxidase activity or other enzyme activity or other biological molecule and which eliminates the need to mix the individual reagents at the time of the test procedure or to change the pH thereof. Further, the present invention is also useful for detecting and quantifying various biological molecules including haptens, antigens and antibodies by immunoassay; proteins by Western blotting; DNA and RNA by Southern and Northern blotting; cholesterol; as well as detecting DNA fragments in DNA sequencing applications The composition hereof is a formulation for use as a substrate in assaying and detection procedures and comprises: (a) at least one chemiluminescent organic compound, (b) an oxidizing agent, (c) a stabilizing agent or stabilizer and (d) a buffer. The present formulation may further include a chemiluminescence enhancer as well as a solubilizer, if necessary.

The oxidizing agent or oxidant is, preferably, a peroxide or an in-situ peroxide generator and which co-acts with peroxidase or other enzyme or other biological compound such as, protein, glucose, DNA, RNA, cholesterol and the like.

The present composition provides chemiluminescent light production from not only peroxidase, but glucose oxidase, cholesterol oxidase, catalase, protohemin, hemoglobin as well as cytochrome C.

The present formulation enables a detection level of 10 femtograms of horseradish peroxidase.

For a more complete understanding of the present invention, reference is made to the following detailed description and accompanying examples.

DETAILED DESCRIPTION OF THE INVENTION

As noted hereinabove, the present invention provides stabilized substrate or reagent formulations for use in assaying peroxidase and other enzyme and biological molecule activity. The present composition may be stored in solution over a long period of time and provides enhanced chemiluminescent sensitivity in assay procedures.

The chemiluminescent assay formulation or substrate of the present invention, generally, comprises:

(a) at least one organic chemiluminescent compound;

(b) an oxidizing agent;

(c) a stabilizing agent or stabilizer, and;

(d) a buffer;

The present composition may further include a chemiluminescent enhancer, as well as a solubilizing agent.

More particularly, the first component in the reagent hereof is the at least one organic chemiluminescent compound. Among the useful organic chemiluminescent compounds which maybe used herein, are, for example, resorcinol, pyrogallol, phloroglucinol, purpurogallin, aminoaryl cyclic diacylhydrazide or the salts thereof, wherein the aryl group maybe phenyl, substituted phenyl, naphthyl, substituted naphthyl, anthryl or substituted anthryl; hydroxyaryl cyclic diacylhydrazide, where the aryl group is phenyl, substituted phenyl, naphthyl, substituted naphthyl, anthryl or substituted anthryl; pyridopyridazine derivatives; acridanes, substituted acridanes, such as 10,10'-dimethy-9, 9'-biacridane, 9-benzylidene-10-methylacridane, substituted-9-benzylidene-10-mrthylacridane, N-methylacridane or substituted N-methylacridane, 9-benzylacridane, substituted-9-benzylacridane, 9-benzyl-N-methylacridane, substituted-9-benzyl-N-methylacridane, N-alkylacridane-9-carboxylic acid, an ester or thioester thereof, indole-3-acetic acid, an ester or thioester thereof, N-methylindole-3-acetic acid, an ester thereof, phenyl or substituted phenyl-2-(6'-hydroxy-2-benzothiazolyl-$\Delta^2$-thiazoline-4-carboxylate, methyl 2-(6'-hydroxy-2'-benzothiazolyl)-$\Delta^2$-thiazoline-4-carboxylate, 2-(6'-hydroxy-2'-benzothiazolyl)-$\Delta^2$-thiazoline acetic acid or an ester thereof, 2-(4'-hydroxyphenyl) thiazole-4-carboxylic acid hydrazide, 2-(6'-hydroxy-2'-benzothiazolyl) thiazole-4-carboxylic acid hydrazide, 9-acridanecarboxylic acid hydrazide, substituted 9-acridanecarboxylic acid hydrazide, N-alkyl-9-acridanecarboxylic acid hydrazide, substituted N-alkyl-9-acridanecarboxylic acid hydrazide, o-hydroxybenzoic acid hydrazide, o-aminobenzoic acid hydrazide, m-hydroxybenzoic acid hydrazide, 2-hydroxy-3-naphthoic acid hydrazide, 2-amino-3-naphthoic acid hydrazide, 1-hydroxy-2-anthroic acid hydrazide, D-luciferin-O-sulfate, D-luciferin-O-phosphate, luciferins isolated from *Pholas dactius*, the firefly *Photinus pyrali* or *Cypridina*, as well as mixtures thereof.

In the practice of the present invention, the preferred chemiluminescent compound is luminol or acridane or mixtures of such chemiluminescent compounds.

The oxidizing agent, which participates in the reaction of the organic chemiluminescent compound with the enzyme or biological molecule to produce chemiluminescence, is either a peroxide or a compound which can produce a peroxide in-situ. Representative oxidizing agents include hydrogen peroxide, urea hydrogen peroxide, sodium carbonate hydrogen peroxide or a perborate salt. Other oxidants or oxidizing agents known to those skilled in the art may be used herein. The preferred oxidant is either hydrogen peroxide or urea hydrogen peroxide and mixtures thereof. As noted systems which produce peroxide in situ can be used such as a D-glucose and glucose oxidase system as well as a cholesterol—cholesterol oxidase system and the like.

The stabilizing agent prevents the peroxide compound from reacting prior to addition of the enzyme or the other molecule to the composition. The stabilizer or stabilizing agent may be selected from any of the well known stabilizers including, for example, cyclodextrin, dextrin sulfate, sugars such as glucose, sucrose and others, nonionic surfactants, such as glycerol, propylene glycol, as well as those well known commercially available ethylene oxide/propylene oxide adducts compounds sold commercially under such names as Tween 20, Tween 40, Tween 60, Tween 80, Tween 85, Triton X-100, Triton X-100 (reduced), Triton N-101, Triton N-101 (reduced), Triton X-114, Triton X-114 (reduced), Triton X-405, Triton X-405 (reduced), Brij 35 and the like; other useful stabilizers include anionic surfactants such as lauryl sulfate, domiphen bromide, cetyltrimethyl ammonium bromide, cetyltrimethyl ammonium chloride, cetyldimethylethyl ammonium bromide (CTAB); proteins, such as bacitracin, BSA, KLH, HSA, Trypsin inhibitor; polymers such as polymeric phosphonium salts and polymeric ammonium salts. Still, other useful stabilizers include those compounds sold under the names DEQUEST 2060S and coenzyme A; as well as inorganic pyrophosphates, cytidine nucleotides, ethylenediaminetetraacetic acid (EDTA), diethylenetriaminepentaacetic acid, ethylene-bis(oxyethylenenitrilo) tetraacetic acid, and other related macromolecules as well as any other compounds capable of stabilizing the chemiluminescent compound in the formulation and which are known to the skilled artisan.

The substrate hereof, preferably, has a pH of about pH 5.5 to about pH12.0. Thus, a buffer is used to bring the substrate within the useful pH range.

Suitable buffers include for example citrates, acetates, tris, borates, carbonates and phosphates, aminopropanols and the like, as well as mixtures thereof. Suitable acids or bases, as needed, can be used to adjust the pH of the buffer or buffers to bring the final pH of the system to pH 5.5 to pH 12.0.

As noted above, the present substrate may, also, include a chemiluminescence enhancer. Generally, the enhancer used herein comprises an organic compound which is soluble in an organic solvent or in a buffer and which enhances the luminescent reaction between the chemiluminescent organic compound, the oxidant and the enzyme or other biological molecule. Suitable enhancers include, for example, halogenated phenols, such as p-iodophenol, p-bromophenol, p-chlorophenol, 4-bromo-2-chlorophenol, 3,4-dichlorophenol, alkylated phenols, such as 4-methylphenol and, 4-tert-butylphenol, 3-(4-hydroxyphenyl) propionate and the like, 4-benzylphenol, 4-(2',4'-dinitrostyryl) phenol, 2,4-dichlorophenol, p-hydroxycinnamic acid, p-fluorocinnamic acid, p-nitroicinnamic acid, p-aminocinnamic acid, m-hydroxycinnamic acid, o-hydroxycinnamic acid, 4-phenoxyphenol, 4-(4-hydroxyphenoxy) phenol, p-phenylphenol, 2-chloro-4-phenylphenol, 4'-(4'-hydroxyphenyl) benzophenone, 4-(phenylazo) phenol, 4-(2'-carboxyphenylaza) phenol, 1,6-dibromonaphtho-2-ol, 1-bromonaphtho-2-ol, 2-naphthol, 6-bromonaphth-2-ol, 6-hydroxybenzothiazole, 2-amino-6-hydroxybenzothiazole, 2,6-dihydroxybenzothiazole, 2-cyano-6-hydroxybenzothiazole, dehydroluciferin, firefly luciferin, phenolindophenol, 2,6-dichlorophenolindophenol, 2,6-dichlorophenol-o-cresol, phenolindoaniline, N-alkylphenoxazine or substituted N-alkylphenoxazine, N-alkylphenothiazine or substituted N-alkylphenothiazine, N-alkylpyrimidylphenoxazine or substituted N-alkylpyrimidylphenoxazine, N-alkylpyridylphenoxazine, 2-hydroxy-9-fluorenone or substituted 2-hydroxy-9-fluorenone, 6-hydroxybenzoxazole or substituted 6-hydroxybenzoxazole. Still other useful compounds include a protected enhancer that can be cleaved by the enzyme such as p-phenylphenol phosphate or p-iodophenol phosphate or other phenolic phosphates having other enzyme cleavable groups, as well as p-phenylene diamine and tetramethyl benzidine. Other useful enhancers include fluorescein, such as 5-(n-tetradecanyl) amino fluorescein and the like. Of course mixtures of enhancers may be used. Herein, the preferred enhancer is p-phenylphenol.

The solubilizing agent increases the solubility of both the enhancer, when used, and the organic chemiluminescent compound in the aqueous buffer solution. When the organic chemiluminescent compound and enhancer are not water soluble any suitable organic solvent such as dimethyl sulfoxide, dimethyl formamide, dioxane, tetrahydrofuran and alcohols may be used with the stabilizers as a solubilizer.

In preparing the present composition, the components are used in the following amounts:

(a) the organic chemiluminescent compound is present in an amount ranging from about 0.1 µM to about 200 mM, and preferably, from about 1.0 µM to about 20 mM, based on the total composition;

(b) the oxidant is present in an amount ranging from about 0.5 µM to about 250 mM, and, preferably, from about 5.0 µM to about 15 mM, based on the total composition;

(c) the stabilizing agent is present in an amount ranging from 0.01% to about 40%, by volume, based on the total volume, and, preferably, from about 0.25 to about 10%, and (d) the buffer is present in an amount ranging from about 0.1 mM to about 10 M and, preferably, from about 1.0 mM to about 2 M based on the total volume.

Where used, the enhancer is present in an amount ranging from about 0.1 µM to about 200 mM, and, preferably, from about 1.0 µM to about 20 mM based on the total volume.

The solubilizing agent, where used, is present in an amount ranging from about 0.1 to about 20%, by volume, based on the total volume and from about 0.5 to about 7.5% by volume, based on the total volume.

The balance of the composition is water or one of the buffers enumerated above, or mixtures thereof.

The substrates of the present invention are ordinarily used at a temperature ranging from about 10° C. to about 50° C., and, preferably, from about 20° C. to about 37° C., and as noted usually, the pH with range from about pH 5.5 to about pH 12.0 and, preferably, at a pH of about pH 7.0 to about pH 9.5.

It should be noted that enzymes, such as, galactosidase and glutonidase can be used to produce enhancers in-situ.

In use the detection limit of the enzyme or enzyme conjugates may vary. In some cases when the enzyme is freshly prepared and in a suitable buffer, the detection limit can be reached at a few femtogram level or even lower level.

The formulations hereof when stored in an amber bottle at room temperature have remained stable several weeks or at 4° C. have remained stable for a period of several months. The stabilized formulations are ready for use at any time an assay is conducted.

Following are specific non-limiting examples. In the examples all parts are by weight absent contrary indications. In carrying out these examples the following ingredients and reaction were used:

MATERIALS AND METHODS

Pyrogallol, phloroglucinol, resorcinol, luminol, isoluminol, 4-phenylphenol, 4-iodophenol, 4-hydroxycinnamic acid, 1,2,4-triazole, 3,3',5,5'-tetramethylbenzidine, phenol, 2-naphthol, 10-methylphenothiazine, cetyltrimethyl ammonium bromide, domiphen bromide, hydrogen peroxide, and urea hydrogen peroxide were purchased from Aldrich, Milwaukee, Wis., USA. Triton X-100 was obtained from Spectrum Chemical Corp., Gardena, Calif., USA. DEQUEST 2060S was obtained from Monsanto Company, St. Louis, Mo., USA. Lauryl sulfate, tris, Tween 20, ethylenediaminetetraacetic acid and glucose oxidase were obtained from Sigma, St. Louis, Mo., USA. Horseradish peroxidase was obtained from Biozyme Laboratories, San Diego, Calif., USA. Polymeric phosphonium and polymeric quaternary ammonium salts were prepared according to the teachings of U.S. Pat. Nos. 3,065,272 and 4,340,522. 5-Hydroxy-2,3-dihydroxyphthalazine-1,4-dione was synthesized according to procedures found in the literature (Emil H. White and Maurice M. Bursey, *J. Org. Chem.*, 31, 1912(1966). Similarly, phenyl-10-methylacridane-9-caboxylate and 2',4', 6'-trichlorophenyl-10-methylacridane-9-carboxylate were prepared according to the teachings of R. Stolle, *J. Prakt. Chem.*, 105, 137 (1922) and M. M. Rahut, D. Sheehan, R. A. Clarke, B. G. Roberts and A. M. Semel, *J. Org. Chem.*, 30, 3587 (1965), F. McCapra, "The Chemiluminescence of Organic Compounds," *Pure Appl. Chem.*, 24, 611 (1970)].

From the above materials, the following test solutions were prepared:

Solution A: a buffer solution prepared by dissolving 19 parts of tris in 1600 parts of deionized (DI) water with the pH of the solution being adjusted to pH 8.5 to pH 8.7 using concentrated hydrochloric acid. Twenty four (24) parts of Triton X-100 is added to the tris solution and stirred at high speed to make the buffer solution homogeneous.

Solution B: Two parts of the selected chemiluminescent compound dissolved in 20 parts of dimethyl sulfoxide (DMSO) and maintained in solution under a nitrogen or argon blanket.

Solution C: Two parts of a selected enhancer dissolved in 20 parts of dimethyl sulfoxide (DMSO) and stored under nitrogen or argon.

Solution D: A buffered horseradish peroxidase enzyme diluted in a buffered enzyme solution in which the enzyme is stable for an extended period of time at room temperature. Solution D was prepared using 10 mg peroxidase enzyme dissolved in 1 ml of a buffer to form the solution. 100 µl of this peroxidase solution is further diluted in 900 µl of a buffer. This resulting solution contains 1 part of peroxidase enzyme in 1000 parts of a buffer. Next 100 µl of this resulting peroxidase enzyme is added to 900 µl of a buffer. This final solution contains 1 part of the peroxidase enzyme in 10,000 parts of buffer or a dilution factor of 10 K.

A series of solutions were prepared from solution D so that the peroxidase enzyme was diluted to 100 K, 1 M, 10 M, 100 M, 1 B, 10 B, 100 B and 1 T, as indicated in the examples below.

Luminescence Measurement

Light intensity measurements were made using a Monolight 2010 single tube (75×12 mm) luminometer. All analytical results are the average of at least duplicate measurements.

EXAMPLE I

A chemiluminescent formulation in accordance herewith was prepared with a solution B containing luminol as a chemiluminescent compound and a solution C containing p-phenylphenol as the enhancer by the following procedure:

To 100 ml of solution A was added 0.6 ml of solution B and 1.0 ml of solution C dropwise with stirring. Next 40 mg of lauryl sulfate was added thereto and stirred for about 5 to 10 minutes. Next, 50 µl of hydrogen peroxide was added thereto dropwise with stirring. A 200 µl sample was transferred into a tube, placed in the luminometer and background luminescence was recorded. Then 10 µl of 1 B enzyme solution was added thereto. The luminescence was recorded at 60 second intervals to a maximum intensity. In this experiment the background was 12, signal intensity was 187341. The signal to background ratio was calculated 15612.

The procedure was repeated but in the absence of the enhancer, a 10 M enzyme solution was used and the background was recorded at 6.1, signal was 436749 and signal/background ratio was calculated 71598.

Figure 1A:
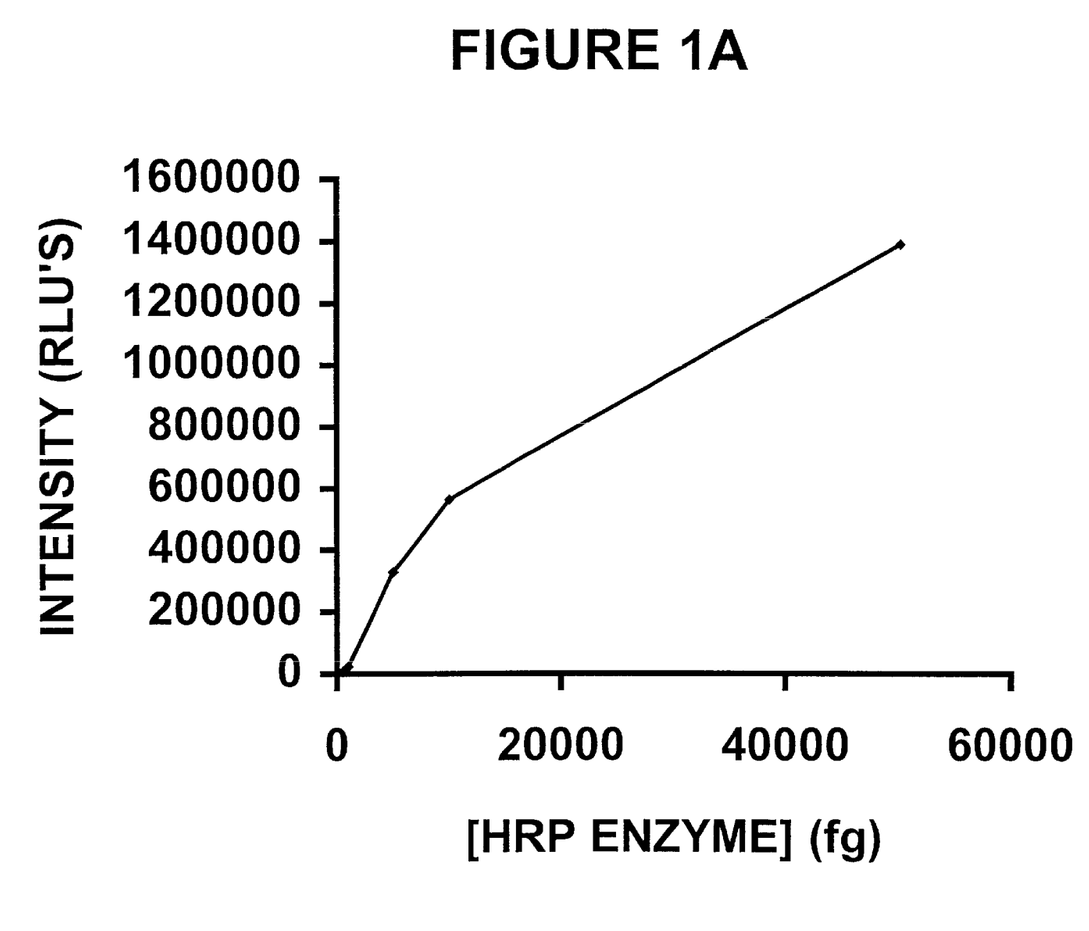
Figure 1B:
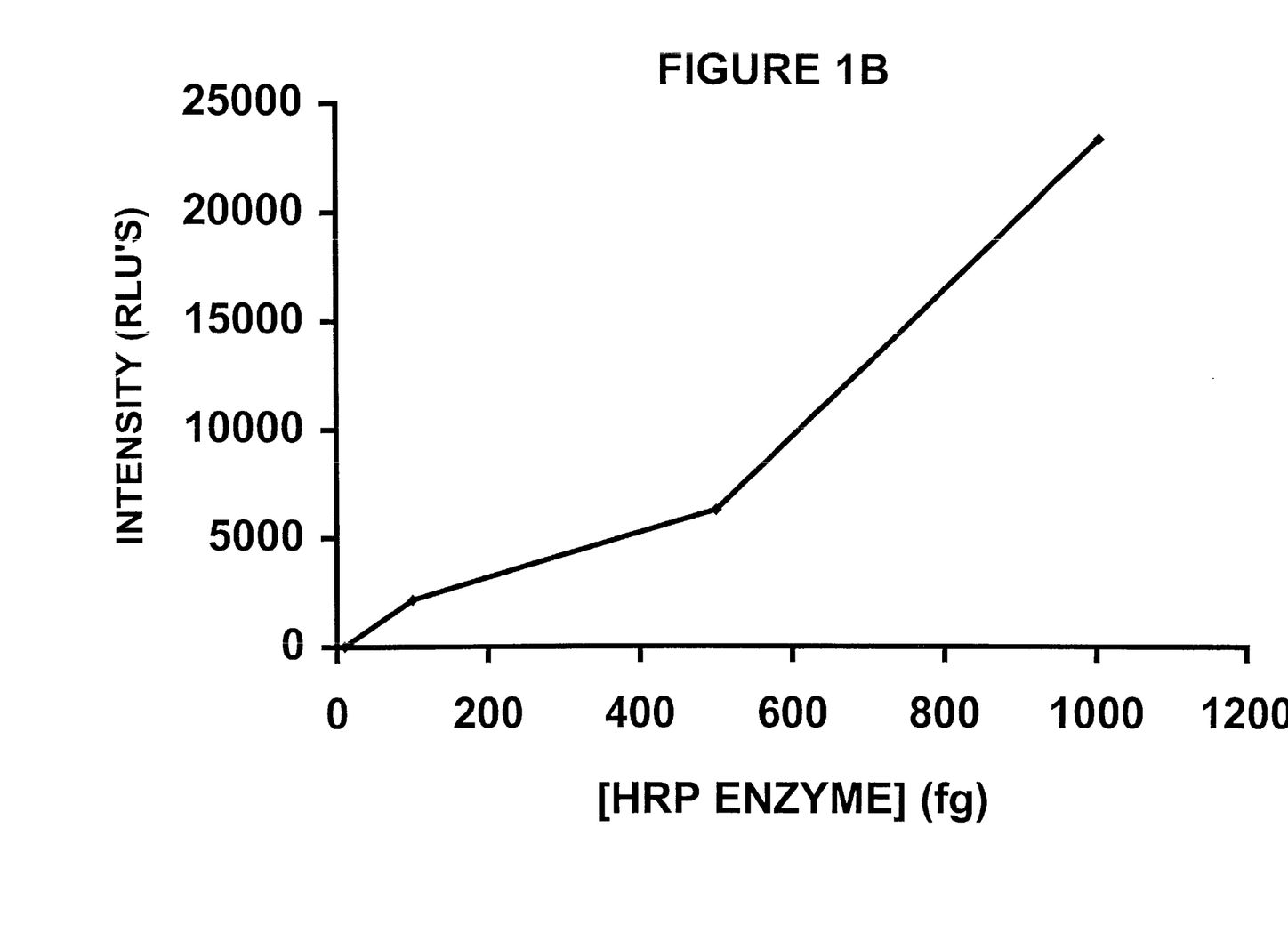

This procedure was repeated using varying concentrations, in femtograms, of peroxidase enzyme and was plotted against intensity. This is shown in FIGS. 1A and 1B, with FIG. 1B showing the lower concentration.

This procedure was further repeated in a series of tests where the lauryl sulfate stabilizer was replaced with the following components and with the following observed results:

| Component | Background | Signal | S/B |
|---|---|---|---|
| domiphen bromide | 6.4 | 223189 | 34873 |
| CTAB | 4.5 | 232782 | 51729 |
| Bacitracin | 3.5 | 106822 | 30520 |
| DEQUEST 2060S | 250 | 55998 | 234 |
| EDTA | 2.1 | 137141 | 65305 |
| 0.5 ml polymeric phosphonium salt | 4.7 | 207051 | 44053 |
| EDTA + lauryl sulfate + 0.5 ml polymeric phosphonium salt | 3.4 | 143684 | 42260 |
| lauryl sulfate + 0.5 ml polymeric phosphonium salt | 5.1 | 234467 | 45973 |
| lauryl sulfate + urea hydrogen peroxide | 5.2 | 175077 | 33668 |
| Lauryl sulfate + 100 mg D-glucose | 4.9 | 20095 | 41010 |
| Lauryl sulfate + 7.0 g Glycerol | 4.9 | 78549 | 16030 |

It is seen from the above that the present invention enables the use of a wide variety of stabilizers without impeding the chemiluminescent properties of the formulation.

EXAMPLE II

A further formulation was prepared using the same solution B and solution C as in Example I. Here solution A contained 0.75 parts of CTAB and 0.01 parts of 5-(N-tetradecanoyl) aminofluorescein. The substrate was prepared as follows: To 100 ml of solution A was added 0.6 ml of solution B and 1.0 ml of solution C dropwise with stirring. Next 40 mg of lauryl sulfate was added thereto and stirred for about 5 to 10 minutes. A 20 µl hydrogen peroxide was added dropwise with stirring. A 200 µl sample was transferred into a tube in the luminometer and background luminescence was recorded. Then 10 µl of 1 B enzyme was added. The luminescence was recorded at 60 second intervals to a maximum intensity. The background was 14, signal intensity was 13093. The signal to background ratio was calculated as 935. When 10 µl of 100 M enzyme was used, the background was recorded as 16, signal intensity was 230220 and signal/background ratio was calculated 14388.

EXAMPLE III

Example I was repeated except that 10 µl of 1 M enzyme was added to the solution after recording the background luminescence and Solution B used resorcinol in lieu of luminol. The luminescence was recorded at 20 second intervals to a maximum intensity. In this experiment the background was 1.9, signal intensity was 2197. The signal to background ratio was calculated as 1156.

EXAMPLE IV

This example illustrates the preparation of another formulation in accordance with the present invention. In this example solution B contains pyrogallol and solution C contains p-phenylphenol.

In preparing the composition, the following procedure was used: To 100 ml of solution A was added 0.6 ml of solution B and 1.0 ml of solution C dropwise with stirring. Next, 40mg of lauryl sulfate was added, and then, stirred for about 5 to 10 minutes. Thereafter 50 µl hydrogen peroxide was added dropwise with stirring. A 200 µl sample was transferred into a tube and placed in the luminometer. Background luminescence was recorded and then 10 µl of 1 M enzyme was added. The luminescence was recorded at 20 second intervals to a maximum intensity. The background was measured as 18 and signal intensity was 8939. The signal to background ratio was calculated as 497.

EXAMPLE V

Following the procedure of Example IV a further formulation was prepared. Herein, solution B contained phloroglucinol and solution C contained p-phenylphenol.

The luminescence was recorded at 20 second intervals to a maximum intensity. The background was 1.9, signal intensity was 2767. The signal to background ratio was calculated as 1456 when the procedure was repeated. In the presence of 5-(N-tetradecanoyl) aminofluorescein added to solution A, the background was 1.9, the signal intensity was 5411 and signal to background ratio was calculated 2848.

EXAMPLE VI

To 100 ml of solution A was added 0.6 ml of a solution B and 1.0 ml of a solution C dropwise with stirring. Then 40 mg of lauryl sulfate was added and stirred for about 5 to 10 minutes. Thereafter, 20 µl hydrogen peroxide was added dropwise with stirring. A 200 µl sample was transferred into a tube and background luminescence was recorded. Then 10 µl of I M enzyme was added thereto. The luminescence was recorded at 60 second intervals to a maximum intensity. In this experiment background was 7.4, signal intensity was 2305. The signal to background ratio was calculated 312.

In this example solution B contained isoluminol and solution C contained p-phenylphenol.

EXAMPLE VII

To 100 ml of solution A was added 0.6 ml of a solution B and 1.0 ml of a solution C dropwise with stirring. Thereafter 40 mg of lauryl sulfate was added and stirred for 5 to 10 minutes. Then, 20 µl of hydrogen peroxide was added dropwise with stirring. A 200 µl sample was transferred in a tube as described above and background luminescence was recorded. Then 10 µl of 1M enzyme was added. The luminescence was recorded at 60 second intervals to a maximum intensity. The background was measured as 63, signal intensity was 8258. The signal to background ratio was calculated as 131.

In this example solution B contained 5-hydroxy-2,3-dehydrophthalazine-1,4-dione and solution C contained p-phenylphenol.

EXAMPLE VIII

The procedure of Example VII was followed except that solution B contained 3-hydroxybenzoic acid hydrazide and solution C contained p-phenylphenol. The luminescence was recorded at 20 second intervals to a maximum intensity. In this example background was 2.0, signal intensity was 1405. The signal to background ratio was calculated as 703.

This procedure was repeated except that 10 µl 5-(N-tetradecanoyl) aminofluorescein solution was added to solution A with the aminofluorescein and the background was 1.9, the signal intensity was 4431 and signal to background ratio was calculated 2332.

EXAMPLE IX

Example VII was repeated except that solution B contained 1,2-bis-3-hydroxybenzoic acid hydrazide and solution C contained p-phenylphenol.

The luminescence without a fluorescein was recorded at 20 second intervals to a maximum intensity. With a background of 2.1, and a signal intensity of 482. The signal to background ratio was calculated 230. In the presence 10 µl of 5-(N-tetradecanoyl) aminofluorescein solution the background was 2.1, the signal intensity was 2656 and signal to background ratio was calculated 1062.

EXAMPLE X

A buffer solution was prepared by dissolving 0.6 g of tris in 200 ml of Dl water. The pH was adjusted to pH 8.0 by addition of hydrochloric acid. Any dissolved oxygen in the buffer was replaced by bubbling nitrogen gas there through for 15 minutes. Then, 10.0 g of Triton X-100 surfactant was dissolved in the solution and the buffer was kept under nitrogen. Next, a solution B containing 40 mg of 2',4',6'-trichlorophenyl-10-methylacridane-9-carboxylate in 1 ml of DMSO was added to the buffer. Then, 1.0 ml of a solution C using p-phenyphenol was added dropwise with stirring. Following this, 40 mg of lauryl sulfate was added and stirred for about ten minutes. Twenty µl of hydrogen peroxide was added dropwise with stirring. A 200 µl sample was transferred to a tube to the luminometer and the background luminescence was measured and recorded. Then, 10 µl of 1 B enzyme was added. The luminescence was recorded at 60 second intervals to a maximum intensity. The background was 3823 and the intensity was 963780. The signal to background ratio was calculated as 252.

Figure 6A:
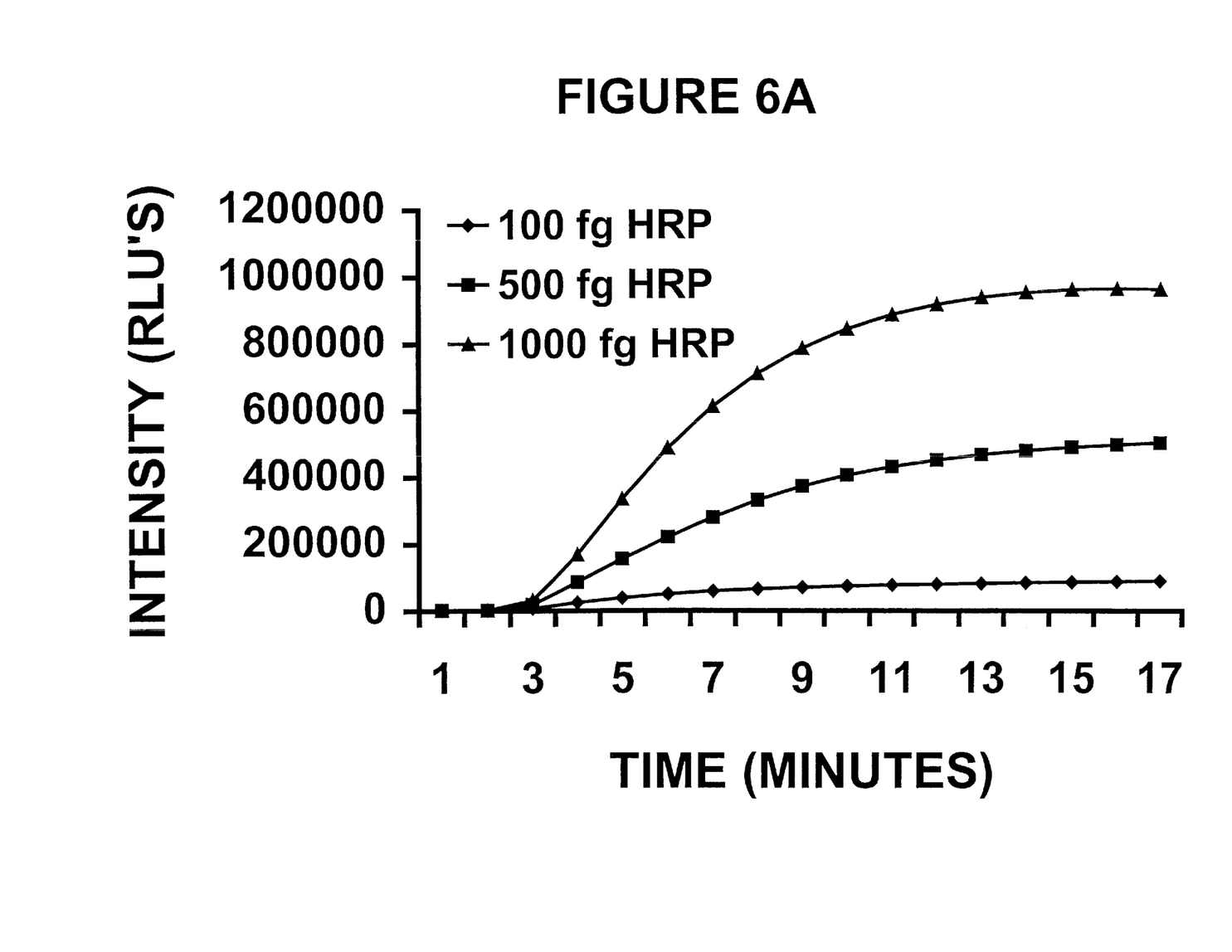
Figure 6B:
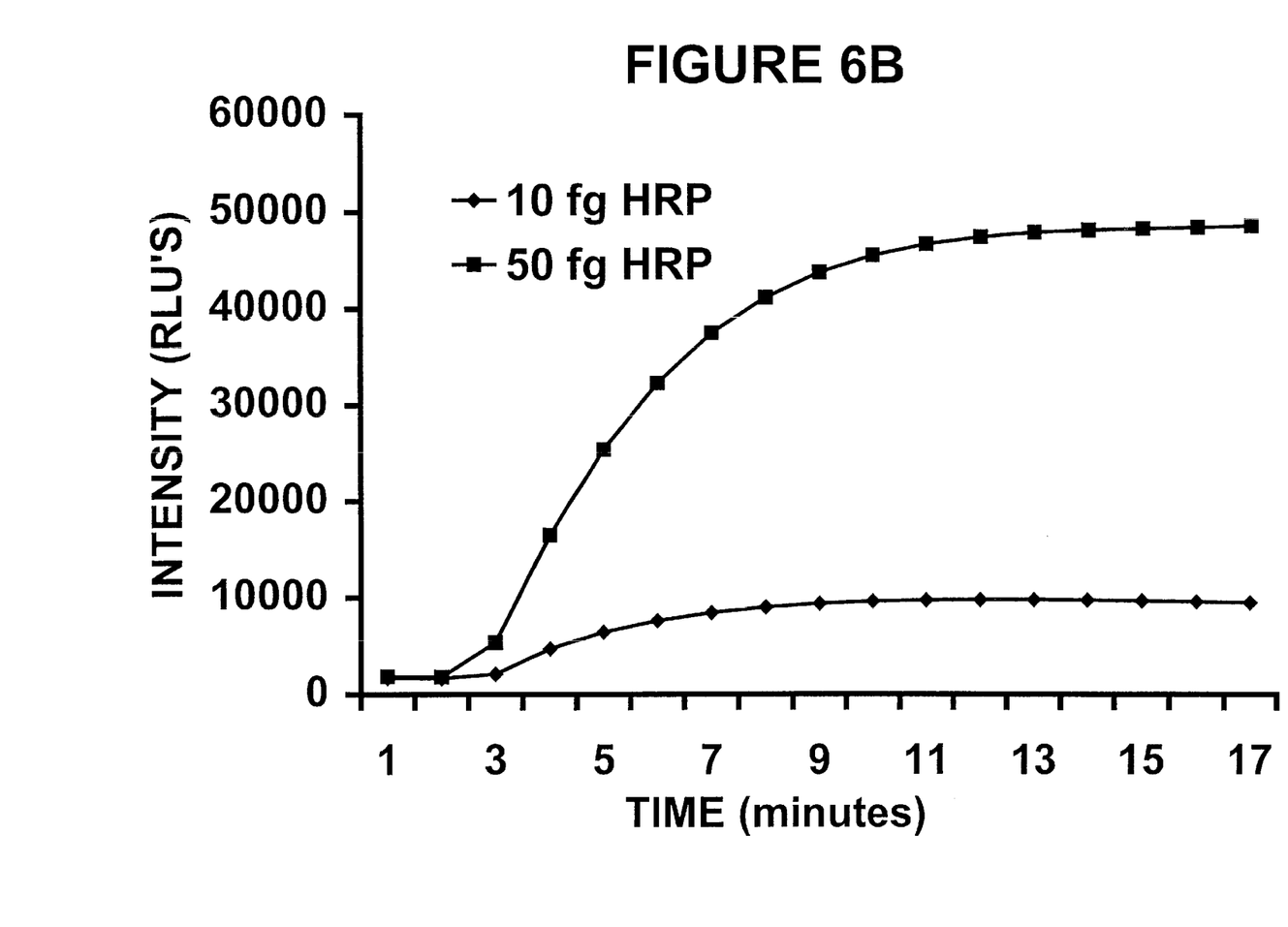
Figure 7:
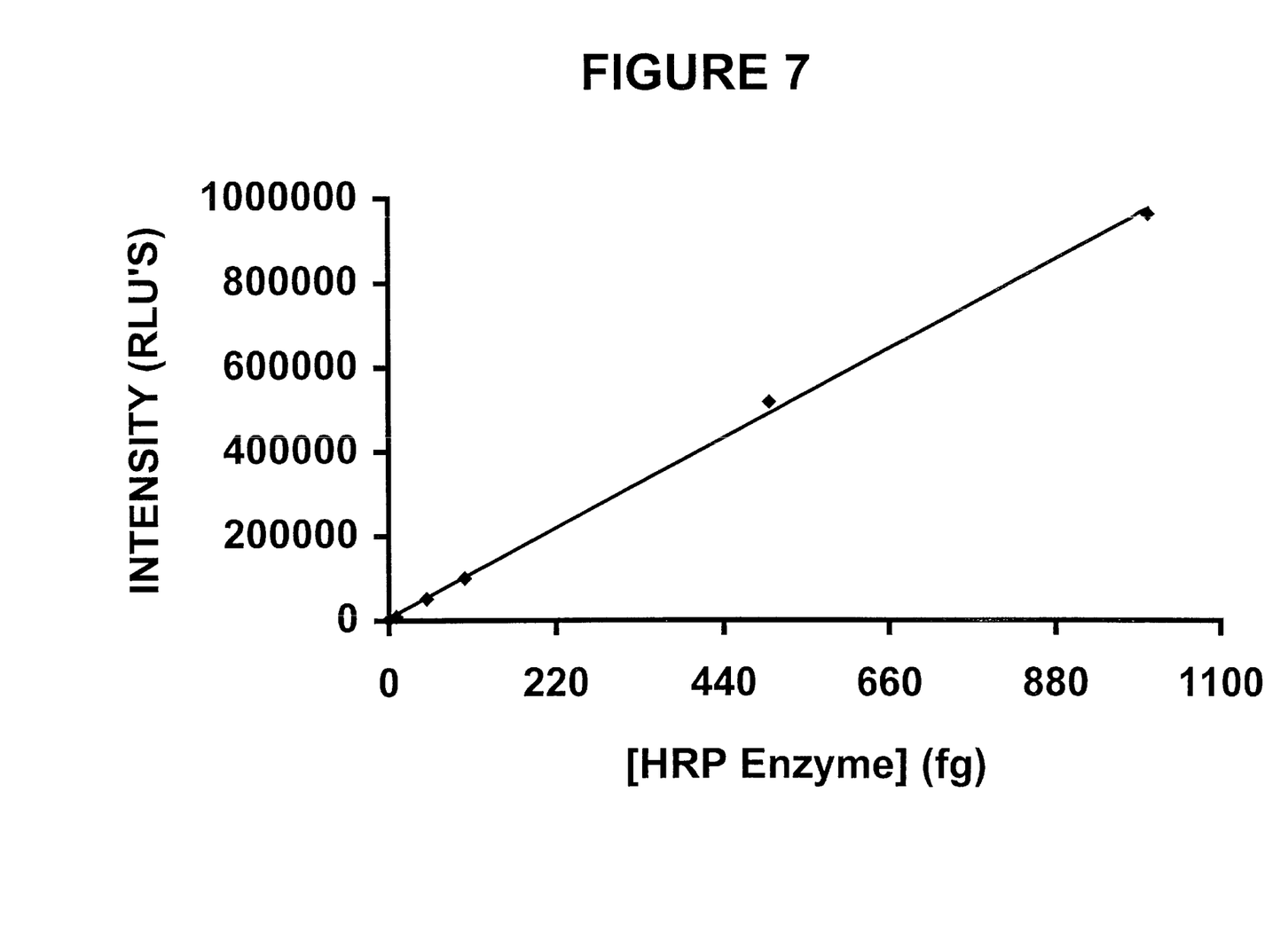

FIG. 6 shows a graph using varying concentrations of the HRP enzyme versus intensity. FIG. 7 plots enzyme concentration versus intensity when the procedure was repeated for varying enzyme concentrations.

EXAMPLE XI

The procedure of Example X was repeated except that 40 mg of phenyl-10-methylacridane-9-carboxylate in 1 ml of DMSO was added to the buffer as the chemiluminescence compound. Luminescence was recorded at 60 second intervals to a maximum intensity. In this example, the background was 2558 and the signal intensity was 1338714. The signal to background ratio was calculated as 523.

EXAMPLE XII

A chemiluminescent formulation was prepared by first preparing a solution A by dissolving 2.29 g of sodium phosphate (dibasic) and 0.528 g of potassium phosphate (monobasic) in 200 ml of Dl water. The pH was adjusted to 8.5 by adding hydrochloric acid thereto. Then, 3.0 g of Triton X-100 surfactant was dissolved in solution A. Here Solution B contained luminol and solution C contained p-phenylphenol. Thereafter, to 100 ml of solution A, 1.2 ml of solution B and 2.0 ml of solution C was added dropwise with stirring. Then, 80 mg of lauryl sulfate was added and stirred for about 8 minutes. Next, 40 µl of hydrogen peroxide was added dropwise with stirring thereto. A 200 µl sample was transferred in a tube into the luminometer and background luminescence was recorded. Thereafter, 10 µl of 1 B enzyme was added. The luminescence was recorded at 60 second intervals to a maximum intensity. In this example, the background was 13.5, and the signal intensity was 241093. The signal to background ratio was calculated as 17859.

EXAMPLE XIII

This example illustrates the efficacy of the present formulation with glucose oxidase as a co-enzyme. Using the same solution A as in Example I, a solution B containing luminol and a solution C containing p-phenylphenol were prepared. Then, 0.6 ml of solution B and 1.0 ml of solution C was added dropwise with stirring to 100 ml of solution A. Next, 40 mg of lauryl sulfate was added and stirred for 5–10 minutes. Then, 0.5 g of D-glucose was added dropwise with stirring. A 200 µl sample was transferred to a test tube. A 10 µl of 1 B enzyme concentration was added to the tube and the background was recorded as described above. Ten µl of a glucose oxidase enzyme solution was added to the test tube and the luminescence was recorded at 60 seconds interval to the maximum intensity. In this example background was 15.1 and signal intensity was 564336. The signal to background ratio was calculated to be 37373. The glucose oxidase solution was obtained by diluting 100 mg of the glucose oxidase enzyme in 3 ml of phosphate buffer at pH 7.4 and, then further diluted by taking 100 μl of the solution and adding it to 1.9 ml of the phosphate buffer.

Figure 2A:
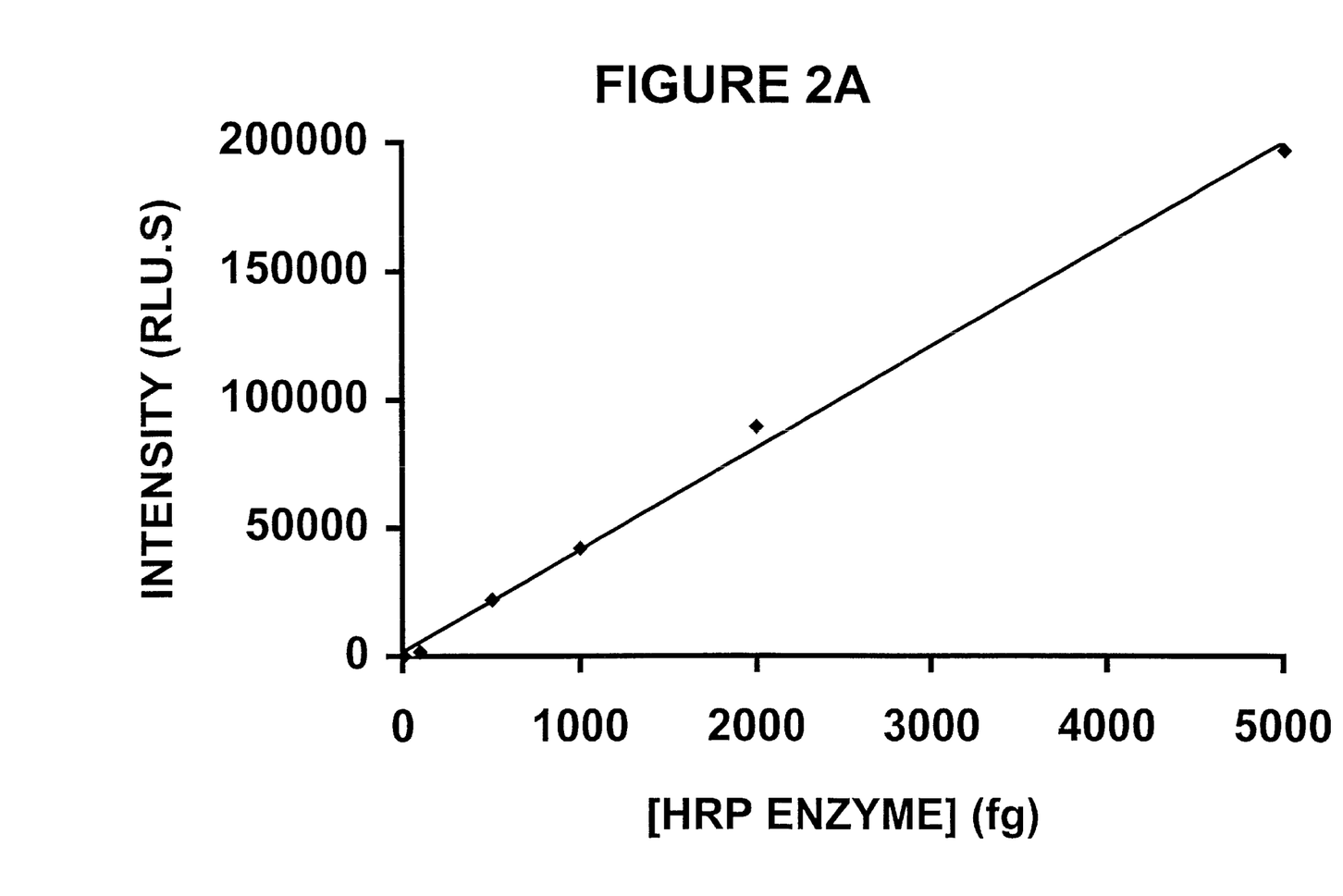
Figure 2B:
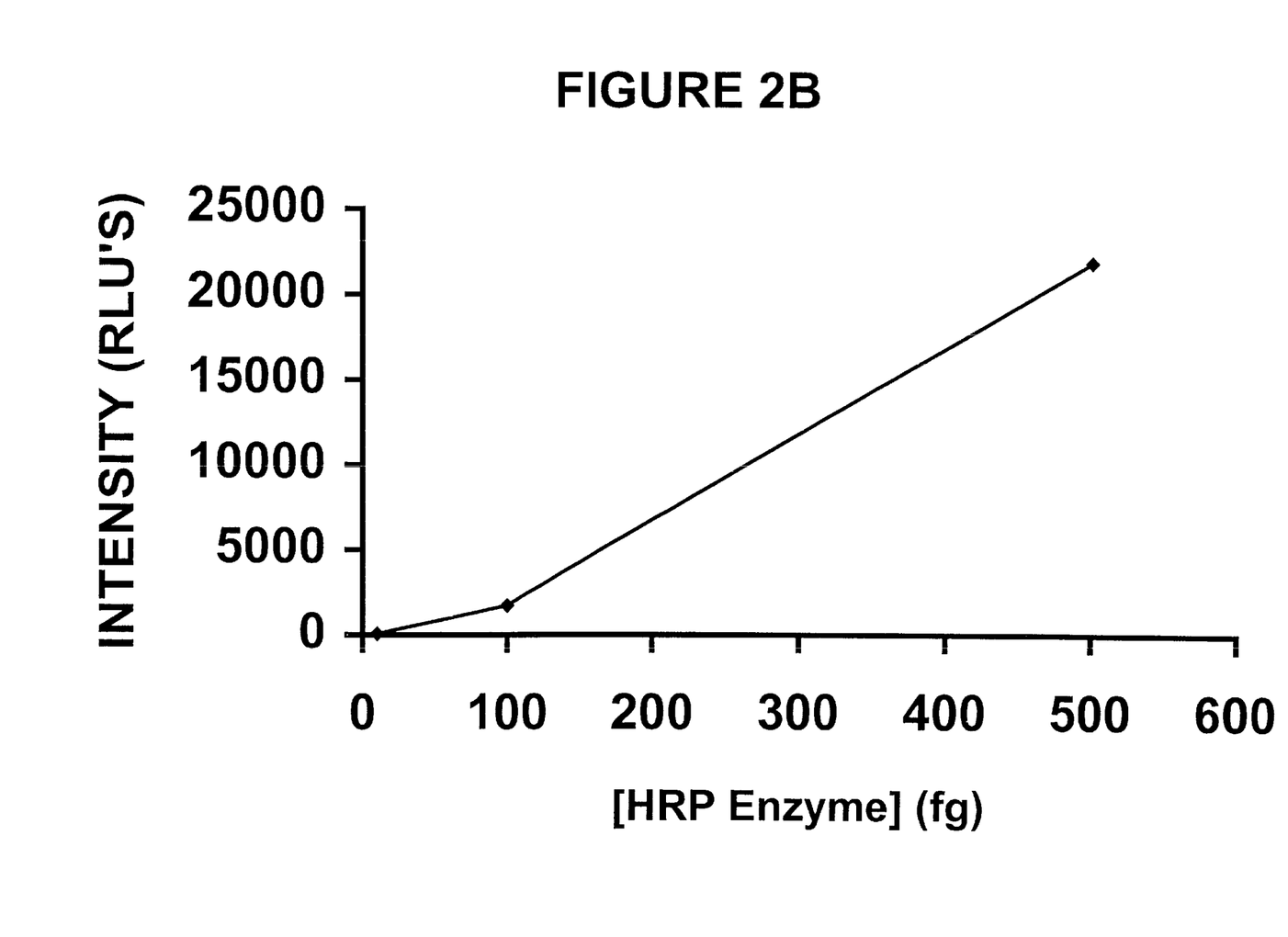
Figure 3:
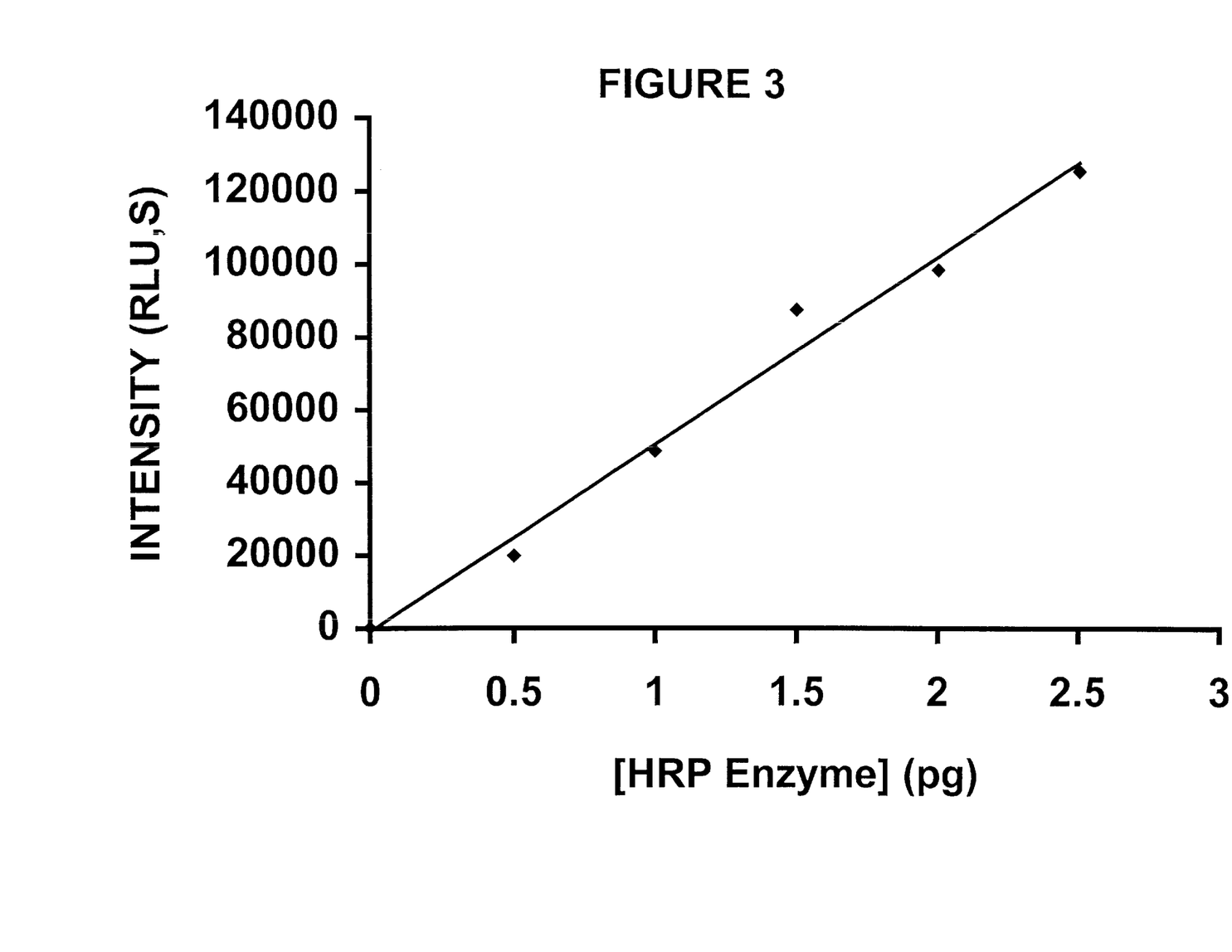
Figure 4A:
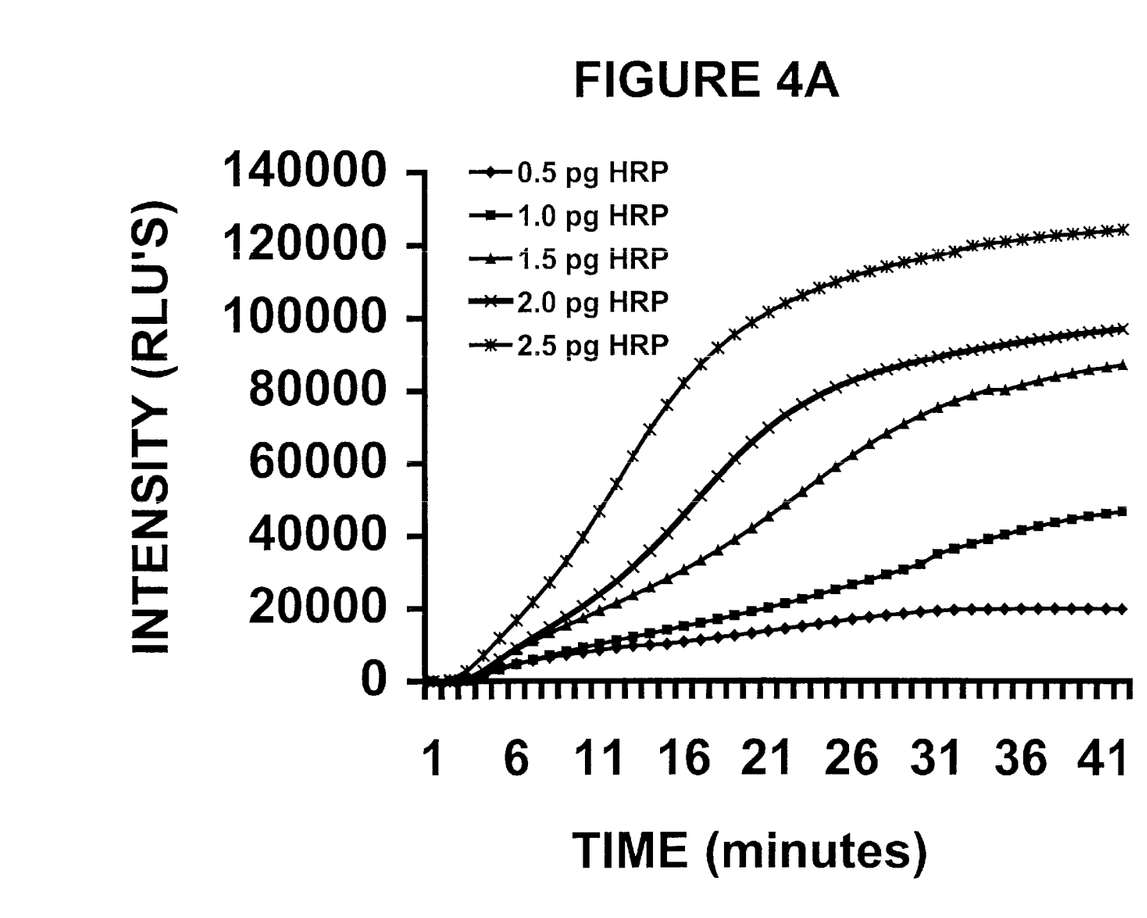
Figure 4B:
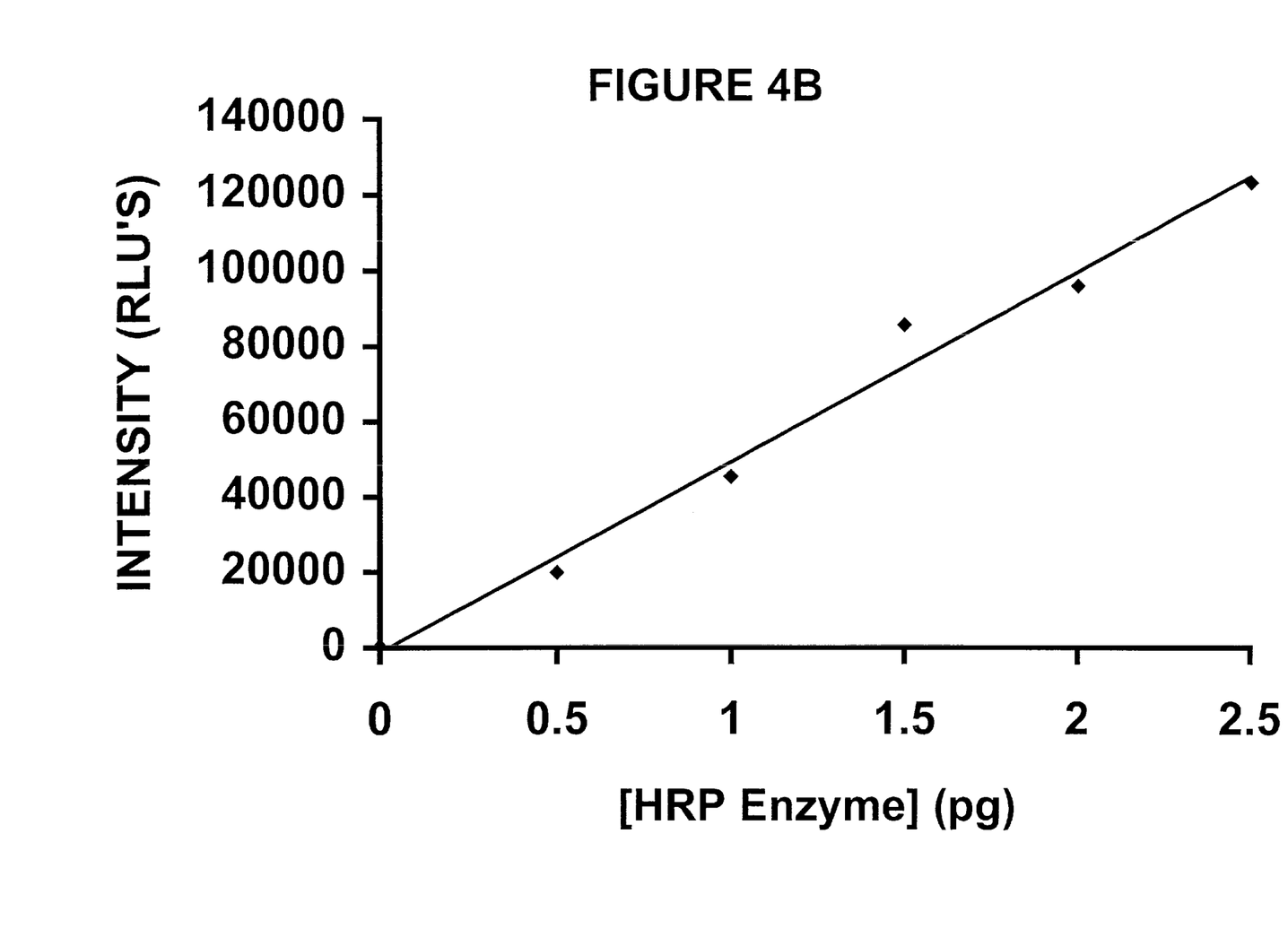

This procedure was repeated using varying concentrations of HRP enzyme and was plotted against measured intensity. This is shown in FIG. 2A and FIG. 2B, with FIG. 2B showing the results at lower concentrations of peroxidase enzyme. FIG. 3 shows linearty of the results over a small range HRP enzyme concentrations, while FIG. 4A shows the time intensity relation for the varying concentrations and 4B shows linearty of the results over a small range peroxidase enzyme concentrations at maximum intensity of light out put.

EXAMPLE XIV

Using the same solution A as in Example I, a chemiluminescent formulation was prepared using a solution B of luminol and a solution C of p-phenylphenol. In preparing the composition 0.6 ml of solution B and 1.0 ml of solution C were added dropwise with stirring to 100 ml of solution A. Then 40 mg of lauryl sulfate, 400 μl of HRP (10K) and 1.0 ml of glucose oxidase were added thereto and stirred for about 5 to 10 minutes.

The glucose oxidase was obtained by dissolving 100 mg thereof in 3 ml of phosphate buffer at pH 7.4. A 200 μl sample was transferred to a test tube and the background was recorded. Thereafter 10 μl of D-glucose (50 mg in 100 ml of DI water) was added to the test tube causing hydrogen peroxide to be generated in-situ. The luminescence was recorded at 10 second of interval to the maximum intensity. In this experiment the background was 1.0 and the signal intensity was 3059.

Figure 5:
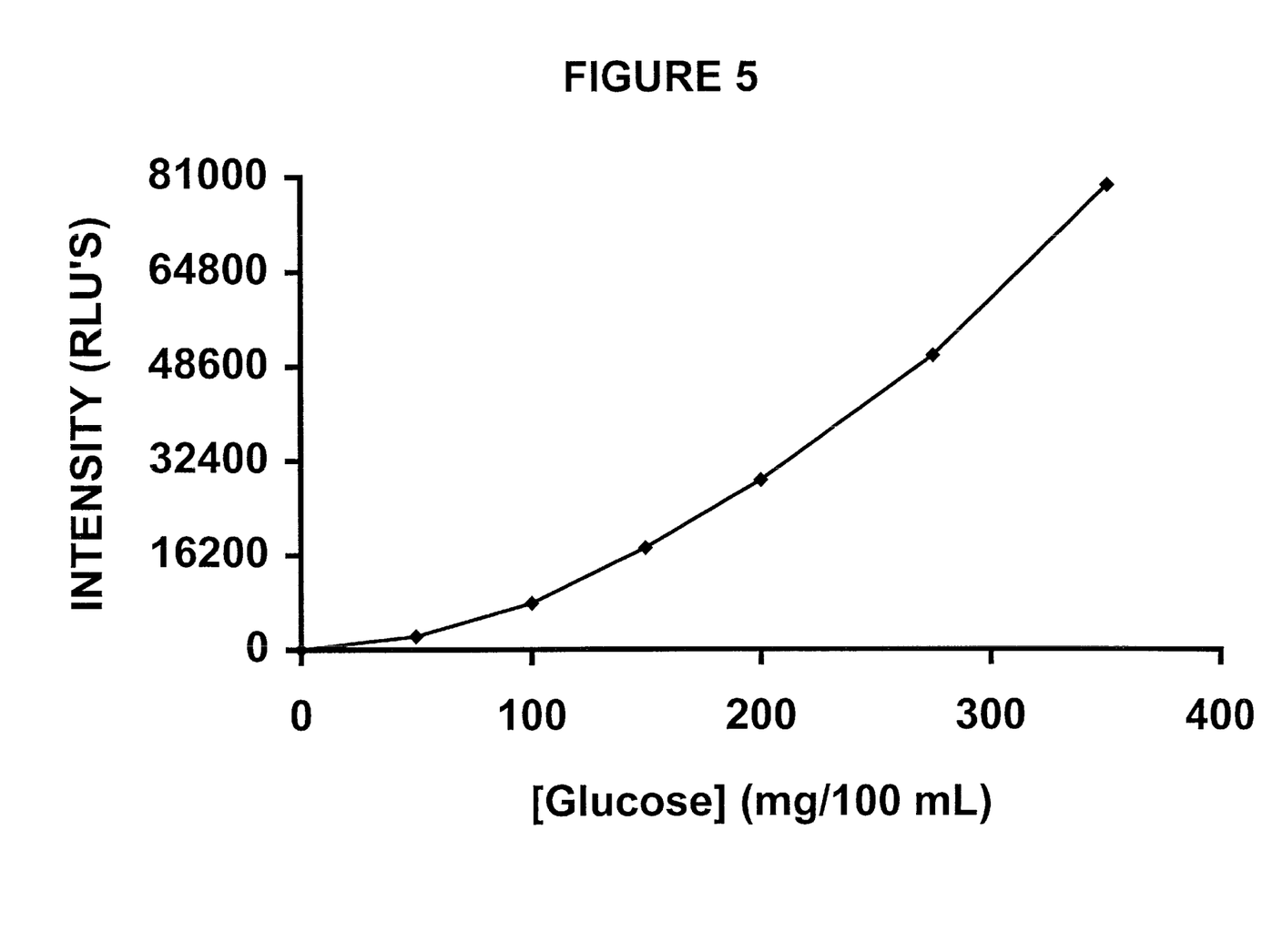

The procedure was repeated using various concentrations of glucose and was plotted against intensity. The results are shown in FIG. 5.

From the above, it is to be readily appreciated that the present invention provides a stabilized chemiluminescent formulation which enables light detection in the presence of peroxide which may be part of the formulation or which can be generated in-situ. It is to be appreciated that by using the horseradish peroxidase, alone, or in conjunction with oxidase enzyme such as glucose oxidase, cholesterol oxidase and the like, the presence of glucose, cholesterol, etc., can readily detected in body fluids such as, blood, serum, saliva, urine and so forth. Similarly, the composition hereof provides a single stable reagent for detecting and quantifying various biological molecules, including haptens, antigens and antibodies by immunoassy; proteins by Western blotting; DNA and RNA by Southern and Northern blotting respectively, and for detecting DNA and for DNA sequencing.

As a detection formulation, the composition hereof defines a substrate. Thus in use, a quantity of known biological molecule such as polyclonal or monoclonal antibody, antigen, hapten-protein, protein, DNA, RNA or the like is deposited or coated onto a support. The support or base is a solid surface which may be of any suitable material such as glass or plastic. The material may be in the form of a microtiter plate or a tube, a bead, a membrane or the like. After the coating is applied, the sample to be tested is then, exposed to the coating, followed thereafter by further sequencing. This can be illustrated as follows:

Where S is the support, Ab is an antibody, Ag is an antigen, Sec. Ab is a secondary antibody, E is an enzyme and the substrate is the present formulation. In the illustration, S-Ab-Ag-Sec.Ab-E defines a probe. Other useful probes include those which correspond to the following:

S-Ag-Ab-Sec.Ab-E;
S-protein-hapten-Ab-E;
S-protein-Ab-E;
S-DNA-biotin-avidin-E; and
S-RNA-biotin-avidin-E.

It is to be appreciated that and in accordance herewith, and as noted above, the enzyme E can be horseradish peroxdase in combination or admixture with glucose oxidase, cholesterol oxidase or the like, or may be an other trigger such as cytochrome C, protohemin, hemoglobin and the like.

Thus, the present invention may be used for, inter alia, labeling haptens, antibodies, proteins, avidin, streptavidin and DNA and RNA for enzyme immunoassays, immunocytochemistry, immunoblotting and DNA detection. Also, the present substrate can be used for detecting cholesterol, or glucose in blood, serum, urine and saliva.

In a commercial embodiment, hereof, the present substrate may be packaged as a kit including a support, as well as, optionally, with an antibody, antigen, secondary antibody, etc. in a separate containers.

Having, thus, described the invention what is claimed is:

1. A method for making a storage stable formulation for use in chemiluminescent assay and detection procedures which comprises:
   (a) mixing together a plurality of compounds consisting essentially of:
      (1) from about 0.1 μM to about 200 mM, of at least one chemiluminescent organic compound,
      (2) from about 0.5 μM to about 250 mM, of at least one oxidizing agent,
      (3) from about 0.01% to about 40%, by volume, based on the total volume, of at least one stabilizing agent, and
      (4) from about 0.1 mM to about 10 mM, of at least one buffer, to form a one-part formulation, the formulation having a pH of from about pH 5.5 to about pH 12.0;
   (b) placing and storing the one-part formulation in an amber bottle, and
      wherein is storage stable for an extended period of time.

2. The method of claim 1 wherein:
   the chemiluminescent compound is selected from the group consisting of resorcinol, pyrogallol, phloroglucinol, purpurogallin, aminoaryl cyclic diacylhydrazide or the salts thereof, hydroxyaryl cyclic diacylhydrazide, pyridopyridazine derivatives, 10,10'-dimethyl-9,9-biacridane, 9-benzylidene-10- methylacridane, substituted-9-benzylidene-10-methylacridane, N-methylacridane, substituted N-methylacridane, 9-benzylacridane, subgtituted-9-benzylacridane, 9-benzyl-N-methylacridane, substituted-9-benzyl-N-methylacridane, N-alkylacridane-9-carboxylic acid, the ester thereof, the thioester thereof, indole-3-acetic acid, the ester thereof, the thioester thereof, N-methylindole-3-acetic acid, the ester thereof, phenyl, phenyl-2-(6'-hydroxy-2-benzothiazolyl)-A²-thiazoline-4-carboxylate substituted phenyl-2-(6'-hydroxy-2-benzothiazolyl-A²-thiazoline-4-carboxylate, methyl 2-(6'-hydroxy-2'-benzothiazolyl)-A²-thiazoline-4-carboxylate, 2-(6'-hydroxy-2'-benzothiazolyl)-A²-thiazoline acetic acid or the ester thereof, 2-(4'-hydroxyphenyl)thiazole-4-carboxylic acid hydrazide, 2-(6'-hydroxy-2'-benzothiazolyl)thiazole-4-carboxylic acid hydrazide, substituted or unsubstituted 9-acridanecarboxylic acid hydrazide, substituted or unsubstituted N-alkyl-9-acridanecarboxylic acid hydrazide or substituted N-alkyl-9-30 acridanecarboxylic acid hydrazide, o-hydroxybenzoic acid hydrazide, o-aminobenzoic acid hydrazide, m-hydroxybenzoic acid hycirazide, 2-hydroxy-3-naphthoic acid hydrazide, 2-amino-3-naphthoic acid hydrazide, 1-hydroxy-2-anthroic acid hydrazide, D-luciferin-O-sulphate, D-luciferin-O-phosphate, luciferins isolated from *Pholas dactlus*, the firefly *Photinus Pyralis* or Cypridina, and mixtures thereof and further wherein when the compound is an aryl compound, the aryl component is phenyl, substituted phenyl, naphthyl, substituted naphthyl, anthxyl or substituted anthryl.

3. The method of claim 1 wherein:
the stabilizing agent is selected from the group consisting of cyclodextrins, a nonionic surfactant selected from the group consisting of polyoxyethylene monolauryl ether, polyoxyethylene sorbitan monolaurate, ethylene oxide condensates of octyl and nonyl phenols, dextrin sulfate, sugars, lauryl sulfate, domiphen bromide, cetyltrimethyl ammonium bromide, cetyltrimethyl ammonium chloride, cetyldimethylethyl ammonium bromide, Bacitracin, BSA, KLH, HSA, Trypsin inhibitor, polyethylene glycol, polymeric phosphonium salts, polymeric ammonium salts, diethylenetriamine penta (methylene phosphoric acid), Coenzyme A, inorganic pyrophosphate s, cytidine nucleotides, ethylenediaminetetraacetic acid, diethylenetriaminepentaacetic acid, ethylene-bis(oxyethylenenitrilo)tetraacetic acid, and mixtures thereof.

4. The method of claim 1 wherein:
the oxidizing agent is selected from the group consisting of hydrogen peroxide, urea hydrogen peroxide, sodium carbonate hydrogen peroxide, a perborate salt and mixtures thereof.

5. The method of claim 1 which further includes:
(a) a solubilizing agent, and
(b) a chemiluminescence enhancer.

6. The method of claim 5 wherein:
(a) the solubilizing agent is present in an amount ranging from about 0.1% to about 20%, by volume, based on the total volume, and
(b) the enhancer is present in an amount ranging from about 0.1 μM to about 200 mM.

7. The method of claim 6 wherein:
(a) the solubilizing agent is selected from the group consisting of dimethyl sulfoxide, dimethyl formamide, dioxane, tetrahydrofuran, alcohols and mixtures thereof, (b) the enhancer is selected from the group consisting of p-iodophenol, p-bromophenol, p-chiorophenol, 4-bromo-2-chlorophenol, 3,4-dichiorophenol, 4-methylphenol, 4-tert-butylphenol, 3-(4-hydroxyphenyl)propionate, 4-benzylphenol, 4-(2',4'-dinitrostyryl)phenol, 2,4-dichlorophenol, p-hydroxycinnamic acid, p-fluorocinnamic acid, p-nitricinnamic acid, p-aminocinnamic acid, m-hydroxycinnamic acid, o-hydroxycinnamic acid, 4-phenoxyphenol, 4-(4'-hydxoxy-phenoxy) phenol, p-phenylphenol, 2-chloro-4-phenylphenol, 4-(4-hydxoxyphenyl)benzophenone, 4-(phenylazo)phenol, 4-(2-carboxyphenylaza)phenol, 1,6-dibromonaphtho-2-ol, 1-bromonaphtho-2-ol, 2-naphthol, 6-bromonaphth-2-ol, 6-hydroxybenzothiazole, 2-amino-6-hydroxybenzothiazole, 2,6-dihydroxybenzothiazole, 2-cyano-6-hydroxybenzothiazole, dehydroluciferin, firefly luciferin, phenolindophenol, 2,6-dichlorophenolindophenol, 2,6-dichlorophenol-o-cresol, phenolindoaniline, N-alkylphenoxazine substituted N-alkylphenoxazine, N-alkylphenothiazine substituted N-alkylphenothiazine, N-alkylpyrimidylphenoxazine substituted N-alkylpyrimidylphenoxazine, N-alkylpyridyiphenoxazine, 2-hydroxy-9-fluorenone, substituted 2-hydroxy-9-fluorenone, 6-hydroxybenzoxazole substituted 6-hydroxybenzoxazole, a protected enhancer for cleaning the enzyme selected from the group consisting of p-phenylphenol phosphate, p-iodophenol phosphate, p-phenylene diamine tetramethyl benzidine and mixtures thereof.

8. The method of claim 1 wherein:
(a) the chemiluminescent compound is selected from the group consisting of luminol, isoluminol, acridane, phenyl-10-methylacridane-9-carboxylate, 2,4,6-trichiorophenyl-10-methylacndane-9-carboxylate, pyrogallol, phioroglucinol, resorcinol, and mixtures thereof,
(b) the oxidizing agent is selected from the group consisting from hydrogen peroxide, urea hydrogen peroxide, an in-situ peroxide forming system, and mixtures thereof, and
(c) the stabilizing agent is selected from the group consisting of polyethylene branched nonylphenyl ether, polyoxyethylene(10)ieooctylphenyl ether, lauryl sulfate, domiphen bromide, CTAB, EDTA and mixtures thereof.

9. A method of stabilizing a composition for use in chemiluminescent assay and detection procedures which comprises:
(a) admixing together a plurality of components consisting essentially of:
(1) from about 0.1 μM to about 200 mM, of at least one chemiluminescent organic compound,
(2) from about 0.5 μM to about 250 mM, of at least one oxidizing agent,
(3) from about 0.01% to about 40%, by volume, based on the total volume, of at least one stabilizing agent,
(4) from about 0.1 mM to about 10 mM, of at least one buffer to form a one-part formulation, the formulation having a pH of from about pH 5.5 to about pH 120,
(b) placing the formulation in an amber bottle, and
(c) storing the formulation in the amber bottle where it remains storage stable for an extended period of time.

* * * * *